United States Patent
Cotton

(10) Patent No.: US 10,086,107 B2
(45) Date of Patent: Oct. 2, 2018

(54) ADHESIVE LAMINATES AND APPLICATIONS THEREOF

(75) Inventor: Stephen Cotton, Nottingham (GB)

(73) Assignee: Brightwake Limited, Nottingham, Nottinghamshire (GB)

( * ) Notice: Subject to any disclaimer, the term of this patent is extended or adjusted under 35 U.S.C. 154(b) by 478 days.

(21) Appl. No.: 12/295,948

(22) PCT Filed: Apr. 3, 2007

(86) PCT No.: PCT/GB2007/050179
§ 371 (c)(1),
(2), (4) Date: Oct. 3, 2008

(87) PCT Pub. No.: WO2007/113597
PCT Pub. Date: Oct. 11, 2007

(65) Prior Publication Data
US 2010/0159192 A1   Jun. 24, 2010

(30) Foreign Application Priority Data
Apr. 3, 2006  (GB) .................................. 0606661.7

(51) Int. Cl.
*B32B 3/24* (2006.01)
*A61L 15/58* (2006.01)
(Continued)

(52) U.S. Cl.
CPC ............ *A61L 15/58* (2013.01); *A61F 13/022* (2013.01); *A61F 13/0213* (2013.01);
(Continued)

(58) Field of Classification Search
CPC ...................................................... C09J 7/0296
(Continued)

(56) References Cited

U.S. PATENT DOCUMENTS

| 2,720,477 A | 4/1953 | Lancaster |
| 2,750,942 A | 6/1956 | Robson |

(Continued)

FOREIGN PATENT DOCUMENTS

| BE | 821734 A1 | 2/1975 |
| CA | 1306701 C | 8/1992 |

(Continued)

OTHER PUBLICATIONS

Colas et al., "Silicone Bipmaterials: History and Chemistry & Medical Applications of Silicones," Biomaterials Science, Second Edition pp. 80-84 and 698-707. (2005).

(Continued)

*Primary Examiner* — William P Watkins, III
(74) *Attorney, Agent, or Firm* — LeClairRyan PLLC

(57) ABSTRACT

A releasably adhesive laminate (1) comprises a structural layer (2) carrying on at least part of one side thereof a hydrophobic gel (4) and on at least part of the other side thereof a pressure-sensitive adhesive (3). The structural layer (2) is preferably a film of synthetic plastics material, eg polyurethane. The pressure-sensitive adhesive (3) is preferably an acrylic adhesive, and the hydrophobic gel (4) is preferably a silicone gel. The laminate (1) may be used as a skin contact component of a wound dressing or in numerous other applications.

11 Claims, 5 Drawing Sheets

(51) Int. Cl.
*A61L 15/42* (2006.01)
*A61F 13/02* (2006.01)
*C09J 7/29* (2018.01)

(52) U.S. Cl.
CPC ...... *A61F 13/0226* (2013.01); *A61F 13/0253* (2013.01); *A61F 13/0259* (2013.01); *A61L 15/42* (2013.01); *C09J 7/29* (2018.01); *C09J 2201/162* (2013.01); *C09J 2433/00* (2013.01); *C09J 2475/006* (2013.01); *C09J 2483/006* (2013.01); *Y10T 428/24322* (2015.01); *Y10T 428/26* (2015.01); *Y10T 428/273* (2015.01); *Y10T 428/2848* (2015.01)

(58) Field of Classification Search
USPC ........................................................ 428/138
See application file for complete search history.

(56) References Cited

U.S. PATENT DOCUMENTS

| | | | |
|---|---|---|---|
| 3,042,549 A | 7/1962 | Arnold et al. | |
| 3,645,264 A | 2/1972 | Gallagher | |
| 4,034,751 A | 7/1977 | Hung | |
| 4,286,592 A | 9/1981 | Chandrasekaran | |
| 4,346,700 A | 8/1982 | Dunshee et al. | |
| 4,353,945 A | 10/1982 | Sampson | |
| 4,423,101 A | 12/1983 | Willstead | |
| 4,427,425 A | 1/1984 | Briggs et al. | |
| 4,550,725 A | 11/1985 | Wishman | |
| 4,598,004 A | 7/1986 | Heinecke | |
| 4,616,644 A | 10/1986 | Saferstein et al. | |
| 4,621,029 A | 11/1986 | Kawaguchi | |
| 4,630,603 A | 12/1986 | Greenway | |
| 4,655,767 A | 4/1987 | Woodard et al. | |
| 4,660,553 A | 4/1987 | Naylor et al. | |
| 4,664,662 A | 5/1987 | Webster | |
| 4,696,854 A | 9/1987 | Ethier | |
| 4,787,380 A | 11/1988 | Scott | |
| 4,815,457 A | 3/1989 | Mazars et al. | |
| 4,838,253 A | 6/1989 | Brassington et al. | |
| 4,867,150 A | 9/1989 | Gilbert | |
| 4,921,704 A | 5/1990 | Fabo | |
| 4,947,877 A | 8/1990 | Meyer et al. | |
| 4,997,425 A | 3/1991 | Shioya et al. | |
| 5,004,465 A | 4/1991 | Ternström et al. | |
| 5,042,466 A | 8/1991 | McKnight | |
| 5,052,381 A | 10/1991 | Gilbert et al. | |
| 5,088,483 A | 2/1992 | Heinecke | |
| 5,123,900 A | 6/1992 | Wick | |
| 5,153,040 A | 10/1992 | Faasse, Jr. | |
| 5,158,555 A | 10/1992 | Porzilli | |
| 5,160,328 A | 11/1992 | Cartmell et al. | |
| 5,167,613 A | 12/1992 | Karami et al. | |
| 5,176,663 A | 1/1993 | Svedman et al. | |
| 5,230,701 A | 7/1993 | Meyer et al. | |
| 5,322,729 A | 6/1994 | Heeter et al. | |
| 5,340,363 A | 8/1994 | Fabo | |
| 5,409,472 A | 4/1995 | Rawlings et al. | |
| 5,415,865 A | 5/1995 | Söderberg et al. | |
| 5,512,041 A | 4/1996 | Bogart | |
| 5,524,765 A | 6/1996 | Gutentag | |
| 5,540,922 A | 7/1996 | Fabo | |
| 5,556,375 A | 9/1996 | Ewall | |
| 5,635,201 A | 6/1997 | Fabo | |
| 5,650,450 A | 7/1997 | Lovette et al. | |
| 5,728,085 A | 3/1998 | Widlund et al. | |
| 5,861,348 A | 1/1999 | Kase | |
| 5,902,260 A | 5/1999 | Gilman et al. | |
| 5,939,339 A | 8/1999 | Delmore et al. | |
| 5,951,505 A | 9/1999 | Gilman et al. | |
| 6,051,747 A | 4/2000 | Lindqvist et al. | |
| 6,231,872 B1 | 5/2001 | Mooney et al. | |
| 6,280,840 B1 | 8/2001 | Luhmann et al. | |
| 6,472,581 B1* | 10/2002 | Muramatsu | A61L 15/26 602/41 |
| 6,479,724 B1 | 11/2002 | Areskoug et al. | |
| 6,486,378 B1 | 11/2002 | Areskoug et al. | |
| 6,541,089 B1 | 4/2003 | Hamerski et al. | |
| 6,566,575 B1 | 5/2003 | Stickels et al. | |
| 6,787,682 B2 | 9/2004 | Gilman | |
| 6,846,508 B1* | 1/2005 | Colas et al. | 427/2.31 |
| 7,066,182 B1 | 6/2006 | Dunshee | |
| 7,161,056 B2 | 1/2007 | Gudnason et al. | |
| 2002/0106471 A1 | 8/2002 | Kuo et al. | |
| 2002/0193723 A1 | 12/2002 | Batdorf, Sr. et al. | |
| 2003/0026967 A1 | 2/2003 | Joseph et al. | |
| 2003/0027475 A1* | 2/2003 | Yu | A63B 49/08 442/149 |
| 2003/0220596 A1* | 11/2003 | Dunshee | 602/42 |
| 2003/0229326 A1 | 12/2003 | Hovis et al. | |
| 2004/0092855 A1 | 5/2004 | Fabo | |
| 2004/0096489 A1 | 5/2004 | Fabo | |
| 2004/0143220 A1 | 6/2004 | Worthley | |
| 2004/0127835 A1 | 7/2004 | Sigurjonsson et al. | |
| 2004/0181198 A1 | 9/2004 | Farbrot et al. | |
| 2004/0249328 A1 | 12/2004 | Linnane et al. | |
| 2005/0059918 A1 | 3/2005 | Sigurjonsson et al. | |
| 2005/0215932 A1 | 9/2005 | Sigurjonsson et al. | |
| 2005/0233072 A1 | 10/2005 | Stephan et al. | |
| 2005/0276965 A1 | 12/2005 | Etchells | |
| 2006/0228318 A1 | 10/2006 | Fabo | |
| 2008/0113572 A1 | 5/2008 | Ragaru et al. | |
| 2010/0267302 A1 | 10/2010 | Katner et al. | |
| 2011/0070391 A1* | 3/2011 | Cotton | 428/43 |
| 2011/0160686 A1 | 6/2011 | Ueda et al. | |
| 2013/0053748 A1 | 2/2013 | Cotton | |

FOREIGN PATENT DOCUMENTS

| | | |
|---|---|---|
| CN | 1775301 A | 5/2006 |
| DE | 2007499 A1 | 9/1971 |
| DE | 3032092 A1 | 4/1982 |
| DE | 3204582 A1 | 8/1983 |
| DE | 3726736 A1 | 2/1988 |
| EP | 0092999 A2 | 11/1983 |
| EP | 0100148 A1 | 2/1984 |
| EP | 0117632 A2 | 9/1984 |
| EP | 0169184 A1 | 1/1986 |
| EP | 0210968 A1 | 2/1987 |
| EP | 0250125 A2 | 12/1987 |
| EP | 0251810 | 1/1988 |
| EP | 0251810 A2 | 1/1988 |
| EP | 0261167 A1 | 3/1988 |
| EP | 0269454 A2 | 6/1988 |
| EP | 0275353 A2 | 7/1988 |
| EP | 0296324 A2 | 12/1988 |
| EP | 0300620 A1 | 1/1989 |
| EP | 0315333 A2 | 5/1989 |
| EP | 0320814 A2 | 6/1989 |
| EP | 0 341 875 A2 | 11/1989 |
| EP | 0342950 A3 | 11/1989 |
| EP | 0355991 A2 | 2/1990 |
| EP | 0356614 A2 | 3/1990 |
| EP | 0 368 541 A1 | 5/1990 |
| EP | 0 375 211 A2 | 6/1990 |
| EP | 0393426 A2 | 10/1990 |
| EP | 0395215 A1 | 10/1990 |
| EP | 0475807 A2 | 3/1992 |
| EP | 0497607 | 8/1992 |
| EP | 0633757 | 1/1995 |
| EP | 0633757 A1 | 1/1995 |
| EP | 0633758 A1 | 1/1995 |
| EP | 0676183 A1 | 10/1995 |
| EP | 0773764 A1 | 5/1997 |
| EP | 0782457 A1 | 7/1997 |
| EP | 0855921 A1 | 8/1998 |
| EP | 0865781 A2 | 9/1998 |
| EP | 0937792 A1 | 8/1999 |
| EP | 0955347 | 11/1999 |
| EP | 0955347 A2 | 11/1999 |
| EP | 1082147 A1 | 3/2001 |
| EP | 1156838 A1 | 11/2001 |
| EP | 1280631 A1 | 2/2003 |
| EP | 1452156 A1 | 1/2004 |

(56) References Cited

FOREIGN PATENT DOCUMENTS

| | | |
|---|---|---|
| EP | 1399145 A2 | 3/2004 |
| EP | 1448128 A2 | 8/2004 |
| EP | 1675536 A2 | 7/2006 |
| EP | 1815875 A1 | 8/2007 |
| EP | 2001424 A2 | 12/2008 |
| FR | 1 151 199 | 1/1958 |
| FR | 1151199 A | 1/1958 |
| FR | 2 528 695 A1 | 12/1983 |
| FR | 2528695 A1 | 12/1983 |
| FR | 2531627 A1 | 2/1984 |
| FR | 2609889 | 7/1988 |
| FR | 2662361 A1 | 11/1991 |
| GB | 498591 A | 1/1939 |
| GB | 713838 A | 8/1954 |
| GB | 735972 A | 8/1955 |
| GB | 741659 A | 12/1955 |
| GB | 781975 | 8/1957 |
| GB | 807276 | 1/1959 |
| GB | 819635 | 9/1959 |
| GB | 821959 A | 10/1959 |
| GB | 833587 A | 4/1960 |
| GB | 898826 A | 6/1962 |
| GB | 950207 A | 2/1964 |
| GB | 987275 | 3/1965 |
| GB | 1018093 A | 1/1966 |
| GB | 1049196 A | 11/1966 |
| GB | 1110016 A1 | 4/1968 |
| GB | 1203611 A | 8/1970 |
| GB | 1282056 A | 7/1972 |
| GB | 1390044 A | 4/1975 |
| GB | 1395815 A | 5/1975 |
| GB | 1398011 A | 6/1975 |
| GB | 1476894 A | 6/1977 |
| GB | 1490065 A | 10/1977 |
| GB | 1494643 A | 12/1977 |
| GB | 1565987 A | 4/1980 |
| GB | 2038661 A | 7/1980 |
| GB | 2074029 A | 10/1981 |
| GB | 2081177 A | 2/1982 |
| GB | 2085305 A | 4/1982 |
| GB | 2153229 A | 8/1985 |
| GB | 2170713 A | 8/1986 |
| GB | 2176401 A | 12/1986 |
| GB | 2186233 A | 8/1987 |
| GB | 2192142 A | 1/1988 |
| GB | 2226780 A | 7/1990 |
| GB | 0606661.7 | 4/2006 |
| GB | 2423267 A | 8/2006 |
| GB | 2425487 | 11/2006 |
| JP | 4312458 A | 11/1992 |
| JP | 10095072 A | 4/1998 |
| JP | 2005029907 A | 3/2005 |
| JP | 2005-314618 | 11/2005 |
| JP | 2005314618 A | 11/2005 |
| SE | 9200983 | 3/1992 |
| SE | 9200984 | 3/1992 |
| SE | 9504077 | 11/1995 |
| WO | WO 87/05206 A1 | 9/1987 |
| WO | WO 88/05269 A1 | 7/1988 |
| WO | WO 90/00732 A1 | 1/1990 |
| WO | WO 90/14109 A1 | 11/1990 |
| WO | WO 91/00718 A1 | 1/1991 |
| WO | WO 91/01706 A1 | 2/1991 |
| WO | WO 91/16059 A1 | 10/1991 |
| WO | WO 92/04923 A1 | 4/1992 |
| WO | WO 92/13576 A1 | 8/1992 |
| WO | WO 93/15249 A1 | 8/1993 |
| WO | WO 93/19709 A1 | 10/1993 |
| WO | WO 93/19710 A1 | 10/1993 |
| WO | WO 94/10953 A1 | 5/1994 |
| WO | WO 94/10957 A1 | 5/1994 |
| WO | 9417765 | 8/1994 |
| WO | WO 94/20054 A1 | 9/1994 |
| WO | WO 94/21207 A2 | 9/1994 |
| WO | WO 95/30394 A1 | 11/1995 |
| WO | WO 96/09076 A1 | 3/1996 |
| WO | WO 96/10972 A1 | 4/1996 |
| WO | 1996031564 A1 | 10/1996 |
| WO | WO 97/11658 A1 | 4/1997 |
| WO | WO 9717922 | 5/1997 |
| WO | WO 97/42985 A1 | 11/1997 |
| WO | WO 97/45146 A1 | 12/1997 |
| WO | WO 98/57677 A1 | 12/1998 |
| WO | WO 99/33420 A1 | 7/1999 |
| WO | WO 99/61077 A1 | 12/1999 |
| WO | WO 99/61078 A1 | 12/1999 |
| WO | WO 99/63920 A1 | 12/1999 |
| WO | WO 00/51650 A1 | 9/2000 |
| WO | 2000065143 | 11/2000 |
| WO | 0168020 | 9/2001 |
| WO | WO 01/85393 A1 | 11/2001 |
| WO | WO 02/20067 A2 | 3/2002 |
| WO | WO 02/28447 A1 | 4/2002 |
| WO | WO 03/39419 A2 | 5/2003 |
| WO | WO 03/079919 A1 | 10/2003 |
| WO | WO 2004/060225 A1 | 7/2004 |
| WO | WO 2004/108175 A1 | 12/2004 |
| WO | 2005021058 | 3/2005 |
| WO | WO 2005/034797 A2 | 4/2005 |
| WO | WO 2005/058381 A1 | 6/2005 |
| WO | WO 2006/075950 A1 | 7/2006 |
| WO | WO 2006/081403 A1 | 8/2006 |
| WO | WO 2006/127292 A1 | 11/2006 |
| WO | 2007025544 | 3/2007 |
| WO | WO 2007/113597 A2 | 10/2007 |
| WO | 2008012443 | 1/2008 |
| WO | WO 2009/047564 A2 | 4/2009 |
| WO | 2010061228 | 6/2010 |
| WO | 2010086457 | 8/2010 |
| WO | 2012028842 | 3/2012 |
| WO | 2012104584 | 8/2012 |

OTHER PUBLICATIONS

Viana et al., "Silicone Versus Nonsilicone Gel Dressings: A Controlled Trial," *Dermatol Surg.* 27(8):721-6 (2001).
Gourlay et al., "Physical Characteristics and Performance of Synthetic Wound Dressings," Trans. Amer. Soc. Artif. Int. Organs vol. XXI:28-33 (1975).
Gourlay et al., "Physical Characteristics and Performance of Synthetic Wound Dressings," Trans. Amer. Soc. Artif. Int. Organs vol. XXI:28-34 (1975).
PCT International Search Report and Written Opinion for corresponding PCT/GB2007/050179 (dated Aug. 21, 2008).
Opposition Against European Patent No. EP 2001424, Opponent Mölnlycke Health Care AB, 28 pages (Aug. 16, 2012).
Declaration of Eric Batelson, Opposition Proceedings regarding EP 2001424, Opponent Mölnlycke Health Care AB, 9 pages (Aug. 14, 2012).
Declaration of Elisabet Ltmdqvist, Opposition Proceedings regarding EP 2001424, Opponent Mölnlycke Health Care AB, 5 pages (Aug. 14, 2012).
Wacker Silicones, Wacker SilGel® 612, data sheet, 3 pages (2004).
Prisma's Abridged English-Swedish and Swedish-English Dictionary, title page, copyright page, pp. 24, 25, 34, 35 (University of Minnesota Press 1998).
Opposition Against European Patent No. EP 2001424, Opponent 3M Innovative Properties Company, 41 pages (Aug. 22, 2012).
Tan et al., "Pressure-Sensitive Adhesives for Transdermal Drug Delivery Systems," *PSTT* 2(2):60-69 (1999).
Handbook of Technical Textiles, title page, copyright page, pp. 4, 13, 130-151 (Horrocks & Anand eds., 2000).
Wikipedia, "Polydimethylsiloxane," webpage http://en.wikipedia.org/wiki/polydimethylsiloxane, 5 pages (Jun. 6, 2012).
Knovel Plastic Material Data Sheet, Dow Corning 7355 Adhesive, 1 page (Kipp ed., 2004).
Inorganic Polymers, title page, copyright page, pp. 4, 5, 61, 62 (DeJaeger & Gleria eds., 2007).
Handbook of Pressure Sensitive Adhesive Technology, cover page, copyright page, pp. 512-517 (D. Satas ed., 2nd ed. 1989).

(56) References Cited

OTHER PUBLICATIONS

Adhesion and Adhesives Technology, The Chemistry and Physical Properties of Elastomer-Based Adhesives, title page, copyright page, pp. 238-241 (A. Pocius ed., 2nd ed. 2002).
Remington: The Science and Practice of Pharmacy, title page, p. 948 (21st ed. 2005).
Thomas, "Silicone Adhesives in Healthcare Applications," Dow Corning Healthcare Industry, 6 pages (2003).
Sample Preparation Handbook for Transmission Electron Microscopy, Introduction to Materials, title page, copyright page, pp. 12-13 (Ayache et al. eds., 2010).
"Milestones in Our History," Screenshot of Mölnlycke Health Care webpage http://www.molnlycke.com/au/About-us/The-Company/AUSNZ/History/Milestones-in-our-History/, 1 page.
"Tendra Startpage>Products>Safetec Technology," Screenshots of archived webpage http://www.tendra.com/item.asp?id=1015&lang=2, Internet Archive: Wayback Machine, 6 pages (Nov. 23, 2003).
"Tendra Startpage>Products>Safetec Technology>Silicone," Screenshots of archived webpage http://www.tendra.com/bottom.asp?id=1869&lang=2, Internet Archive: Wayback Machine, 3 pp. (May 5, 2003).
"Tendra Startpage>Products> Safetec Technology>Dressings," Screenshots of archived webpage http://www.tendra.com/bottom.asp?id=1021&lang=2, Internet Archive: Wayback Machine, 8 pages (May 3, 2003).
"Tendra Startpage>Products>Alphabetical List>Multiplex®Border," Screenshots of archived webpage http://www.tendra.com/item.asp?id=774&pid=558, Internet Archive: Wayback Machine, 3 pages (May 11, 2003).
Tendra, Mepilex® Border Product Sheet, 2 pages (accessed via Internet Archive: Wayback Machine, archived webpage http://www.tendra.com/item.asp?id=774&pid=558, Related Links, Product Sheet) (May 11, 2003).
David D. Johnson, Ph.D., Analytical Report Concerning MEPILEX™ Border Product from Manufacture LOT 3894-01F18, Opposition Proceedings regarding EP 2001424, Opponent 3M Innovative Properties Company, 16 pages (Jul. 6, 2012).
Declaration of David R. Holm, Opposition Proceedings regarding EP 2001424, Opponent 3M Innovative Properties Company, 1 page (Aug. 17, 2012).
Declaration of David D. Johnson, Opposition Proceedings regarding EP 2001424, Opponent 3M Innovative Properties Company, 1 page (Aug. 12, 2012).
Declaration of Clas Bolander, MSc, Sourcing Director, Wound Care Division, Mölnlycke Health Care AB, Opposition Proceedings regarding EP 2001424, Opponent 3M Innovative Properties Company, 1 page (Aug. 13, 2012).
Opposition Against European Patent No. EP 2001424, Opponent Lohmann & Rauscher GmbH & Co. KG, 23 pages (Aug. 23, 2012).
Thomas, "World Wide Wounds-Atraumatic Dressings," www.worldwidewounds.com/2003/january/Thomas/Atraumatic-Dressings.html, 11 pages (2003).
Declaration of Stephen Thomas, Ph.D., Opposition Proceedings regarding EP 2001424, Opponent Lohmann & Rauscher GmbH & Co. KG, 54 pages (Aug. 20, 2012).
Medika AG, Mölnlycke Health Care, price list, 2 pages (2004).
Davies, "Milestones in the Management of Wound Trauma and Pain," Poster Presentation, European Wound Management Association Conference, Glasgow, United Kingdom (2007).
D.E. Packham, Packham Handbook of Adhesion, title page, copyright page, pp. 25-27, 363-365 (2nd ed. 2005).
Handbook of Adhesive Technology, title page, copyright page, pp. 847-848 (Pizzi & Mittal eds., 2003).
Polymer Science, Inc., "Medical," webpage http://www.polymerscience.com/medical.html, 2 pages (Accessed Aug. 17, 2012).
Thomas, X., "Silicones in Medical Applications," Chapter 2.17 in Inorganic Polymers, 12 pages (De Jaeger & Gleria eds., 2007).
Benedek & Heymans, Pressure Sensitive Adhesives Technology, cover page, copyright page, p. 128 (1997).

Declaration of Dr. Thomas Pontzen, Opposition Proceedings regarding EP 2001424, Opponent Lohmann & Rauscher GmbH & Co. KG, 2 pages (Aug. 23, 2012).
Opposition Against European Patent No. EP 2001424, Opponents Gerhard Schmitt-Nilson, Stefan Waibel, 37 pages (Aug. 23, 2012).
Thomas & Mitchell, "Adhesive Technologies for Attaching Medical Devices to the Skin," *Medical Device Technology*, pp. 12-15 (Sep. 2004).
Quinn, "Silicone Gel in Scar Treatment," *Burns* 13:S33-S40 (1987).
Musgrave et al., "The Effect of Silicone Gel Sheets on Perfusion of Hypertrophic Burn Scars," *Journal of Burn Care and Rehabilitation* 23(3): 208-214 (2002).
Wikipedia, "Pressure-Sensitive Adhesive," webpage http://en.wikipedia.org/w/index.php?title?Pressure-sensitive_adhesive&oldid?499251304, 4 pages (Jun. 25, 2012).
Wacker Chemie AG, "Wacker SilGel®, The Specialist for Sensitive Devices," 1 page(2012).
Joe McMahon, M.SC., "Microstructural and Chemical Characterization of Mepilex Border Wound Dressing," Report, Opposition Proceedings regarding EP 2001424, Opponents Gerhard Schmitt-Nilson, Stefan Waibel, 11 pages (Aug. 20, 2012).
Kirit Amin, "Characterization of Mepilex Border by 1H NMR Spectroscopy," Report, Opposition Proceedings regarding EP 2001424, Opponents Gerhard Schmitt-Nilson, Stefan Waibel, 6 pages (Aug. 22, 2012).
amazon.com, "ScarAway Professional Grade Silicone Scar Treatment Sheets," webpage, 2 pages (Aug. 20, 2012).
Mitchell-Vance Laboratories, "ScarAway®: The Solution for Scars™," webpage http://www.scaraway.us, product information, 1 page (Aug. 23, 2012).
acne4idiots.com, "ScarAway Professional Grade Silicone Scar Treatment Sheets," webpage, 4 pages (Aug. 23, 2012).
epinions.com, "Neosporin Scar Solution Silicone Scar Sheets 28 Each," webpage, 3 pages (Aug. 23, 2012).
Opposition Against European Patent No. EP 2001424, Supplement to Facts and Submissions of Notice of Opposition, Opponents Gerhard Schmitt-Nilson, Stefan Waibel, 4 pages (Oct. 29, 2012).
Kirit Amin, "Characterization of Mepilex Border by 1H NMR Spectroscopy," Supplemental Report, Opposition Proceedings regarding EP 2001424, Opponents Gerhard Schmitt-Nilson, Stefan Waibel, 11 pages (Aug. 2012).
Joe Mcmahon, M.SC., "Microstructural and Chemical Characterization of Silicone Scar Sheet," Interim Report, Opposition Proceedings regarding EP 2001424, Opponents Gerhard Schmitt-Nilson, Stefan Waibel, 5 pages (Sep. 11, 2012).
Kirit Amin, "NMR Report on Characterization of Silicone Scar Sheet," Supplemental Report, Opposition Proceedings regarding EP 2001424, Opponents Gerhard Schmitt-Nilson, Stefan Waibel, 10 pages (Sep. 2012).
Joe Mcmahon, M.SC., "Chemical Characterization of Glue and Polymer Layers in Wound Dressings," Final Report, Opposition Proceedings regarding EP 2001424, Opponents Gerhard Schmitt-Nilson, Stefan Waibel, 10 pages (Oct. 2, 2012).
Opposition Against European Patent No. EP 2001424, Response to Request for Documents, Opponents Lohman & Rauscher GmbH & Co. KG, 2 pages (Oct. 29, 2012).
McCulloch, "The History of the Development of Melt Blowing Technology," *International Nonwovens Journal*, 11 pages (1999).
Bresee & Ko, "Fiber Formation During Melt Blowing," *INJ Summer*, pp. 21-28 (2003).
Farer et al., "Study of Meltblown structures Formed by Robotic and Meltblowing Integrated System: Impact of Process Parameters on Fiber Orientation," *INJ Winter*, pp. 14-21 (2002).
Zhao, "Melt Blown Dies: A Hot Innovation Spot," *INJ Winter*, pp. 37-41 (2002).
Starr, The Nonwoven Fabrics Handbook, Association of the Nonwoven Fabrics Industry, Cary, North Carolina, pp. iii-v, 4, 7, 45-62 (Batra et al. eds. 1992).
Kirk Cantor, Blown Film Extrusion: An Introduction, Hanser Gardner Publications, Inc., Cincinnati, Ohio (2006).
Gantner et al., "Soft Skin Adhesive Gels and Liners: New Formulating Options for Tailored Solutions," Dow Corning Corporation (2007).

(56) References Cited

OTHER PUBLICATIONS

United Kingdom Intellectual Property Office, Search Report for Application No. GB0908057.3 (dated Sep. 4, 2009).
PCT International Search Report and Written Opinion for PCT/GB2009/050500 (dated Jul. 22, 2009).
Ulman & Thomas, "Silicone Pressure Sensitive Adhesives for Healthcare Applications" in Handbook of Pressure Sensitive Adhesive Technology-2, Ch. 6, pp. 133-157 (D. Satas ed. 1995).
Blackwood, "Achieving Functional Excellence with Silicone Coatings," Dow Corning Corporation, 8 pages (2004).
Dow Corning® 7-9700 Soft Skin Adhesive Kit (A&B) Product Description, Typical Properties, https://www.dowcorning.com/applications/search/products/Details.aspx?prod= 04035943&type=prod, 1 page (retrieved Jan. 6, 2016).
Dow Corning® 7-9800 Soft Skin Adhesive Kit (A&B) Product Description, Typical Properties, http://www.dowcoming.com/applications/search/defaultaspx?R=1059EN, 1 page (retrieved Jan. 6, 2016).
Viscosity Tables, V&P Scientific Inc, http://www.vp-scientific.com/Viscosity_Tables.htm, 3 pages (retrieved Jan. 6, 2016).
Prof. W. Woebcken, Kunststoff Lexicon, title page, copyright page, pp. 418-419 (1998).
"Milestones in Our History," Screenshot of Mölnlycke Health Care webpage, http://www.molnlycke.com/au/About-us/The-Company/AUSNZ/History/Milestones-in-our-History/, 1 page (Aug. 23, 2012).
A. Vasel-Biergans & W. Probst, Wundauflagen für die Kitteltasche, 4 pages (2nd ed. 2006).

\* cited by examiner

ADHESIVE LAMINATES AND APPLICATIONS THEREOF

This application is a U.S. national stage entry under 35 U.S.C. § 371 of International Patent Application No. PCT/GB2007/050179, filed Apr. 3, 2007, which claims priority from Great Britain Patent Application No. 0606661.7, filed Apr. 3, 2006.

This invention relates to a releasably adhesive laminate suitable for use in a wide variety of applications, in particular for use against the skin and more particularly as part of a wound dressing.

Different types of wound dressing are required to meet different clinical needs. However, there are several desirable characteristics that are common to all wound dressings. Pain-free removal and the ability to remove a dressing without trauma to the wound and the surrounding skin are two of the most important characteristics. In order to prevent pain and trauma, the facing layer of a wound dressing needs to maintain a moist layer over the wound to prevent adherence to the drying wound. However, it is also desirable for a wound dressing to include some form of adhesive layer to maintain it in position. Island dressings are typically used, which comprise a so-called "non-adherent" or "low-adherent" absorbent pad with an adhesive retention layer over the top forming an adhesive border that sticks to skin surrounding the wound. However, repeated removal and replacement of such dressings can damage the peri-wound skin, ie the wound adjacent to the skin. The term "atraumatic dressing" is used in relation to products that, upon removal, do not cause trauma either to newly formed tissue or to the peri-wound skin.

Soft silicone adheres readily to dry skin but does not stick to the surface of a moist wound and does not cause damage on removal. As well as satisfying these principal requirements for use as the skin contact layer in atraumatic dressings, there are several other intrinsic properties of soft silicone that make it particularly advantageous for use in wound dressings. These properties are well-documented and include the fact that silicones are non-toxic, non-allergenic or sensitising, do not shed particles or fibres into the wound, feel soft on the skin and are conformable yet robust.

Numerous published papers describe the properties of silicone and the use of soft silicone dressings. Indeed, there are different types of soft silicone dressings currently on the market, including atraumatic wound contact layers, absorbent dressings for exuding wounds and also a dressing for the treatment of hypertrophic scars and keloids.

EP-A-0633758 discloses a wound dressing comprising a layer of hydrophobic silicone gel, a layer of carrier material and an absorbent body, wherein the carrier material and gel layer have mutually coinciding penetrating perforations at least within the region of the absorbent body.

EP-A-0855921 relates to dressings comprising a layer of absorbent foam. The surface of the foam that is applied to the wound has a pattern of pores or holes and is coated with silicone such that the walls of the holes are coated (without blocking the holes).

EP-A-0300620 describes a surgical dressing, particularly adapted to the treatment of burns, comprising a sheet of silicone gel having a wound-facing surface and laminated to the other surface a film of silicone elastomer.

EP-A-0633757 is concerned with methods by which a dressing comprising a perforated carrier coated with silicone can be manufactured. That method involves blowing cold air onto the underside of the carrier to prevent silicone clogging the perforations.

An absorbent dressing made from polyurethane foam is sold under the trade name Mepilex®. The outer surface of the foam is bonded to a vapour-permeable polyurethane membrane that acts as a barrier to liquids and micro-organisms. The inner surface of the foam is coated with a layer of soft silicone.

An absorbent, self-adhesive island dressing with a perforated soft silicone wound contact layer is sold under the trade name Mepilex Border®. The absorbent core consists of three components: a thin sheet of polyurethane foam, a piece of non-woven fabric, and a layer of super-absorbent polyacrylate fibres.

Another commercially available product, sold under the trade name Mepilex Transfer®, consists of a thin sheet of a hydrophilic open-cell polyurethane foam, coated on one surface with a layer of soft silicone and presented on a plastic film carrier.

The product sold under the trade name Mepitel® is a porous, semi-transparent wound contact layer consisting of a flexible polyamide net coated with soft silicone.

EP-A-0261167 describes an elastic, hydrophobic, knitted network coated with silicone gel.

There is an ongoing need to provide improved wound dressings. No single wound dressing product is suitable for use in all wound types or at all stages of healing. However, the use of soft silicone as the skin contact layer is beneficial in many applications and it would clearly be advantageous to provide a silicone component for use as the skin contact layer in a variety of wound dressings.

Moreover, it would be advantageous to provide a component that can be used as the skin contact layer in a variety of dressings, wherein that component becomes an integral part of the dressing, ie is affixed in such a way that the dressing retains its composite structure when removed.

There has now been devised a hydrophobic gel-bearing laminate that is useful as the skin contact layer for a wide variety of wound dressings, and which furthermore has numerous other applications.

According to a first aspect of the invention there is provided a releasably adhesive laminate comprising a structural layer carrying on at least part of one side thereof a hydrophobic gel and carrying on at least part of the other side thereof a pressure-sensitive adhesive.

The structural layer most preferably has the form of a relatively thin film of a synthetic plastics material. A wide variety of plastics may be suitable for use as the structural layer. Examples include polyvinylchloride, polypropylene and regenerated cellulose. However, the currently preferred material for the structural layer is polyurethane, and in particular melt-blown polyurethane.

The pressure-sensitive adhesive may be any one of numerous pressure-sensitive adhesives known in the art. Such adhesives generally in dry (solvent free) form are aggressively and permanently tacky at room temperature and firmly adhere to a variety of dissimilar surfaces upon mere contact without the need for more than finger or hand pressure. They require no activation by water, solvent or heat in order to exert a strong adhesive holding force. Examples of pressure sensitive adhesives include rubber/resin adhesive, which is a mixture of a rubbery material and a hard resin, and acrylic (or acrylate) adhesives. The currently preferred class of pressure-sensitive adhesive for use in the present invention is acrylic adhesive.

The laminate of the present application provides a simple and versatile means of releasably securing an item to a substrate. Soft silicones (silicone gels) are known to have releasably adhesive properties. The hydrophobic gel that is carried on one side of the structural layer is thus most preferably a silicone gel.

Most preferably, suitable silicone gels are formed by reaction between two components that are mixed immediately prior to application to the structural layer. Suitable components that are intended for such reaction to form a silicone gel are readily available commercially. Typically, the two components are a vinyl substituted silicone and a hydride-containing silicone.

Gels having different properties may be produced by varying the proportions and/or nature of the components used in the reaction. For example, the molecular weights of the various components and/or their degree of substitution by reactive groups may be different.

Suitable components for forming silicone gels for use in the laminate of the present invention are readily available.

The hydrophobic gel may be coated onto the structural layer at a wide variety of coating weights. The most appropriate coating weight will depend on the properties of the gel and its intended application. Typically, the gel may be coated onto the structural layer at a weight of between 50 $g/m^2$ and 800 $g/m^2$. The thickness of the gel may typically be between 5 µm and 10 mm, more commonly between 20 µm and 5 mm.

The properties of silicone gels are well-documented and provide several advantages for the use of silicone gel as the releasably adhesive hydrophobic gel layer in the laminate of the present invention, for many intended applications. For example, silicone gels are soft, tactile and conformable. They are adhesive but do not leave fibres, residue or tack on a surface/substrate when removed.

In particular, silicone gels exhibit excellent releasable adhesion to the skin. The advantages and benefits of skin contact layers comprising layers of silicone gel are particularly well-documented for wound dressing applications. They include softness, good adhesion to dry skin and, particularly importantly, low adherence to an underlying wound. Thus, the dressing can be applied to a wound and subsequently removed without causing trauma to the wound.

Thus, in a related aspect of the invention, there is provided a skin contact layer for use in a dressing, which skin contact layer comprises a structural layer carrying on at least part of one side thereof a hydrophobic gel and carrying on at least part of the other side thereof a pressure-sensitive adhesive.

The adhesive that is applied to the other side of the structural layer may be any one of numerous pressure-sensitive adhesives. One particular example is an acrylic adhesive.

The presence of the pressure-sensitive adhesive on the opposite side of the structural layer to the hydrophobic gel greatly facilitates the assembly of composite dressings that include the laminate. In particular, the presence of the pressure-sensitive adhesive enables secondary dressing components, for instance absorbent materials, to be attached to the laminate, and also fluid-impermeable barrier layers to prevent escape of fluid such as wound exudate from the dressing. Such a composite dressing, including a layer of hydrophobic gel, may retain its integrity upon removal from the skin, enabling the dressing to be removed and repositioned readily. The dressing according to the invention may particularly be an absorbent dressing, ie a dressing that includes an absorbent body capable of absorbing fluids such as wound exudate. Examples of suitable absorbent components that may be incorporated into such a dressing include fabric pads, hydrophilic foams, (in particular polyurethane foam), hydrogels, hydrocolloids and alginates. In such forms of dressing, the absorbent body will generally be positioned adjacent to the side of the laminate that carries the pressure-sensitive adhesive, or will be attached to the laminate by that adhesive.

In order for fluid to be transmitted to the absorbent body, therefore, it will generally be necessary for the laminate to be apertured or perforated. This may also improve the adhesion of the laminate to the skin, as the apertures or perforations permit the escape of fluid, which therefore does not build up under the laminate. Additional advantages of perforation of the laminate include ease of removal, improved flexibility and conformity, and skin breathability.

In one group of presently preferred embodiments of the invention, the laminate is formed with a regular array of perforations. Typically, such perforations are circular and have a diameter of from 50 µm to 10 mm, more commonly from 1 mm to 5 mm.

In some embodiments of a composite dressing in which the side distal to the skin contact layer comprises a fluid-impermeable barrier layer, the barrier layer may be provided with an opening to which is bonded a coupling by which the dressing may be connected to a gas supply or to a suction line. Typically, such a coupling comprises a unitary component that is moulded in plastics material, and includes a tubular connector to which a gas or suction line can be fitted. By this means, air or oxygen can be supplied to the dressing, in order to oxygenate the wound and improve healing, or fluid can be drawn from the dressing, thereby preventing buildup of excessive amounts of fluid within the dressing.

Prior to use, the layer of hydrophobic gel is most preferably protected by a release liner that is removed to expose the hydrophobic gel immediately prior to use. The release liner is most preferably formed in such a way as to be readily grasped and removed, eg by having one or more projecting tabs.

The need for suitable means, such as a bandage, to keep the absorbent pad and/or barrier layers in place over the skin-contact layer is reduced and in many cases removed by the use of dressings according to the invention. With less or no bandaging required, the dressing is easier to apply and remove, and more comfortable for the patient. The advantages of the laminate layer being an integral part of the dressing, and removal of the need for bandaging, may allow the dressing to be changed by a patient or helper, when otherwise the expertise of a medical practitioner or other experienced professional would be required to apply the dressing.

Wound dressings of the present invention may be preformed in manufacture or may be made up by a medical practitioner in an extemporaneous manner for specific applications or for a particular patient. Alternatively, a composite dressing can be assembled after first applying only the laminate. This approach may be particularly useful in situations where the dressing is awkward to position correctly and/or accurate positioning is particularly vital, for whatever reason. The laminate is preferably supplied with release liners protecting both the pressure-sensitive adhesive layer and the hydrophobic gel layer. The release liner would be removed from the hydrophobic gel layer and the hydrophobic gel placed over the wounds such that it overlaps the wound margin. The release liner covering the pressure-adhesive layer can then be peeled back and a secondary dressing component affixed to form the composite dressing.

Manufactured dressings according to the invention will generally be packaged as individual units in envelopes that are bacteria-proof and which are sterilized, most commonly using ethylene oxide or by irradiation with γ-radiation.

Apart from its use in wound dressings, the laminate of the present invention is useful for numerous other applications in which the hydrophobic gel layer contacts the skin. Silicone gels exhibit excellent releasable adhesion to the skin and it is therefore preferred that the hydrophobic gel layer is a silicone gel for those applications too.

Thus, according to another aspect of the invention there is provided an item intended to be affixed to the skin of a user, to which item is attached, via the pressure-sensitive adhesive, a patch of a laminate according to the first aspect of the invention.

In these skin contact applications, it is again preferable for the laminate to be apertured or perforated. Perforations improve adhesion with the skin because moisture, eg sweat, is transmitted away from the skin rather than accumulating under the laminate and consequently reducing adhesion. Likewise, the perforations improve skin breathability. The ease of removal of the laminate is improved by perforating the laminate because the perforations reduce the area of hydrophobic gel that is in direct contact with the skin. Perforations also enhance the flexibility and conformity of the laminate.

One form of skin-contact application in which the laminate of the present invention is useful is in the affixing of items of clothing to the skin. Such items of clothing may be items of outerwear, but more commonly are items of underwear. For instance, the laminate may have a form suitable for application to a bra or the like. Such an arrangement may reduce or eliminate the requirement of additional fastenings such as straps or clasps. The laminate may thus be incorporated into strapless and/or backless bras. In a similar manner, the laminate may be applied to a component that functions simply as a nipple cover. The laminate may also find application in securing other items of underwear, such as ladies' stockings.

The laminate may also be applied to items of outerwear, such as dresses or strapless "tops", in order to hold such items in position, for instance where a dress or other item of clothing has a revealing neckline.

The laminate is also useful for securing wigs, false beards or moustaches and the like. The laminate may offer several advantages over conventional tapes used for the same purpose, including softness on the skin, improved conformability and breathability. Particular benefits may include the ease and comfort of removal and the ability to remove and reposition with little or no loss of adherence.

Another potential field of application for the laminate according to the invention is in the securing to the body of protective or other equipment used in sports or outdoor activities. The laminate may be affixed to the equipment via the pressure-sensitive adhesive, such that the hydrophobic gel-bearing surface is, in use, applied to the user's skin. The laminate may then provide for, or enhance, the correct positioning of the equipment on the body. Examples of protective equipment to which the laminate may be applied include shin, knee or elbow guards. The laminate may also be applied to an item of sports equipment that, in use, is grasped by a user, in order improve the user's grip on that equipment, or which is fitted to a user's hand. Examples of such equipment include bats, eg for cricket or baseball, racquets for use in tennis, badminton or squash, and golf clubs, and also catching gloves, as used in sports such as cricket and baseball.

In yet further applications of the laminate according to the invention, it is used not for the application of articles to the skin, but for releasably securing items to hard surface substrates. Thus, according to a yet further aspect of the invention, there is provided an item intended to be affixed to a hard surface substrate, to which item is attached, via the pressure-sensitive adhesive, a patch of a laminate according to the first aspect of the invention.

In such applications, the laminate may be attached via the pressure-sensitive adhesive to the substrate, so that the hydrophobic gel-bearing side of the laminate constitutes a patch onto which the item to be secured can be placed.

Alternatively, the laminate may be applied to the item. In either case, the laminate constitutes a means for adhering the item to the substrate. The degree of adherence may vary considerably, depending in particular on the nature of the substrate and the item, and of the hydrophobic gel. The item may be secured to the substrate relatively strongly, such that the item does not move in normal usage. Where the degree of adherence is less strong, the hydrophobic gel-bearing side of the laminate may simply act as a non-slip surface that inhibits, without necessarily completely preventing, movement of the item relative to the substrate.

The laminate may be used in innumerable applications in the home and workplace, and also in cars or other vehicles. For instance, the laminate may be used to fix an item such as a mobile phone to the fascia or dashboard of a car or other vehicle.

The laminate according to the invention may be manufactured in various ways. A currently preferred method of manufacture comprises the steps of:
  a) providing a preformed pre-laminate comprising the structural layer and the pressure-sensitive adhesive;
  b) applying to the pre-laminate a curable hydrophobic gel precursor composition; and
  c) causing or allowing the gel precursor composition to cure, thereby forming a layer of hydrophobic gel.

Where the hydrophobic gel is a silicone gel, the hydrophobic gel precursor composition is preferably prepared by mixing immediately prior to application to the structural layer. Typically, such a composition will comprise a vinyl substituted silicone and a hydride-containing silicone.

Embodiments of the invention will now be described in greater detail, by way of illustration only, with reference to the accompanying drawings, in which FIG. 1 is a partial cross-sectional view, schematic and not to scale, of a laminate according to the invention;

Figure 1:
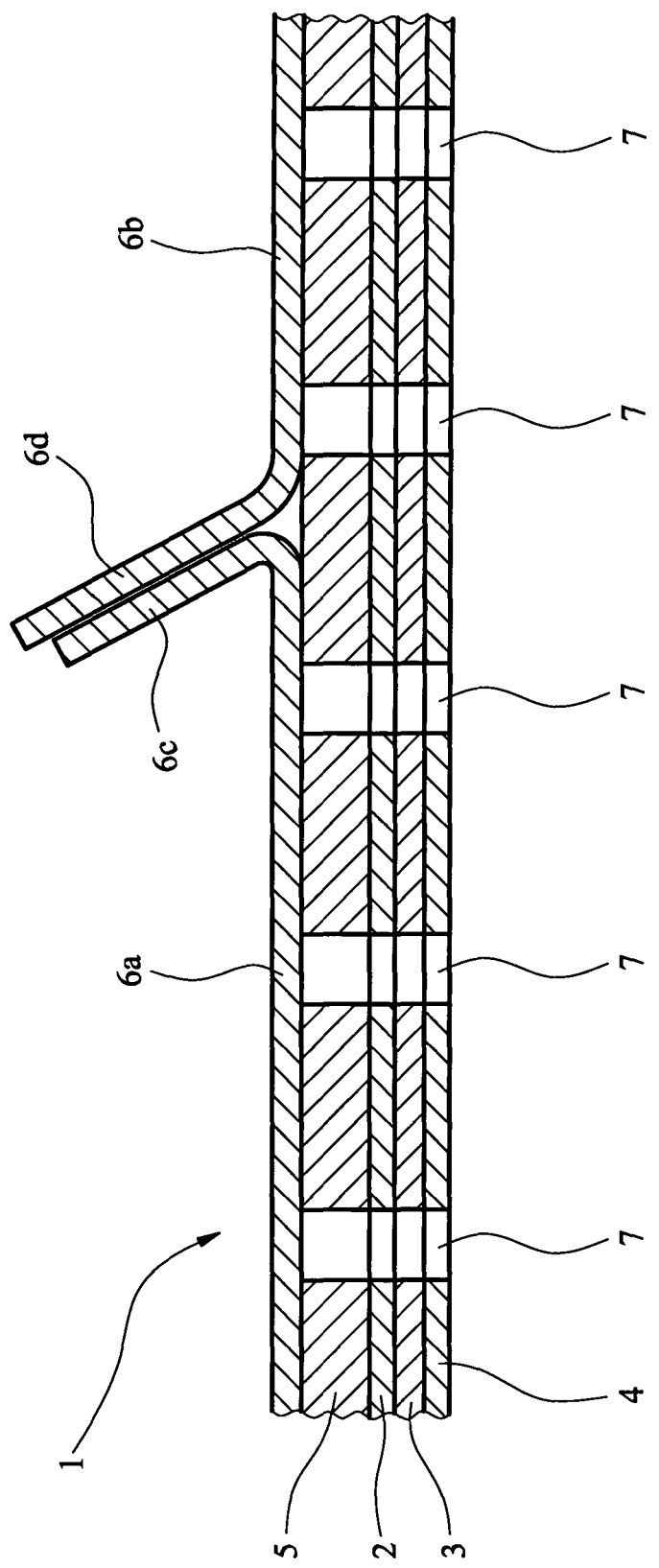

Referring first to FIG. 1, a laminate according to the invention is generally designated 1. The laminate 1 is useful as the skin contact film in a composite wound dressing, as described below, but also in numerous other applications. The laminate 1 comprises a structural layer 2 in the form of a film of melt-blown polyurethane. The structural layer 2 is coated on one side (the underside as viewed in FIG. 1) with a layer of acrylic contact adhesive 3, which in turn carries a paper (or paper/film laminate) backing 4. On the other side (the upper side as viewed in FIG. 1) the structural layer 2 carries a layer of hydrophobic silicone gel 5. The silicone gel layer 5 may have a thickness that varies widely, depending on the form and intended use of the laminate 1 or of a composite article, eg a dressing, that the laminate 1 is incorporated into. The thickness of the silicone gel layer 5 may be as little as 5 μm, but more commonly will be of the order of 20-15 μm or greater, and may be as much as several millimetres, eg 3-4 mm.

A two-part release liner 6a,6b is applied to the upper (as viewed in FIG. 1) surface of the silicone gel layer 5. The release liner 6a,6b is typically formed from high density polyethylene (HDPE). The two components 6a,6b of the release liner overlap, with a fold being formed in one of them 6a so as to create a first tab 6c that is upstanding from the laminate 1 and the other 6b overlying the first tab 6c so as to form a second tab 6d. The tabs 6c,6d can be grasped by a user to enable the components of the release liner 6a,6b to be peeled away from the silicone gel layer 5 prior to application of the silicone gel layer 5 to a substrate.

The laminate 1, formed by the structural layer 2, the acrylic adhesive layer 3, the paper backing 5 and the silicone gel layer 5 is perforated, having a regular array of perforations 7. The perforations 7 may vary considerably in size and shape, again depending on the form and intended use of the article that the laminate 1 is incorporated into, but are typically circular, with a diameter of the order of a few millimetres, eg 2-4 mm, though smaller and larger diameter perforations may be appropriate in certain applications. Usually, the perforations will all be of the same shape and size, but different forms of perforation may be present in the same product. Most commonly, the perforations are arranged in a regular array, the separation between adjacent perforations typically being comparable with, or greater than, the diameter of the perforations. However, an irregular or random distribution of perforations may also be possible.

As shown in FIG. 1, the release liner 6a,6b is not perforated, as it is applied to the silicone gel layer 5 after the perforations 7 have been formed. However, it is also possible for the perforations to be formed after application of the release liner 6a,6b, in which case the release liner 6a,6b would be perforated.

The laminate 1 may be manufactured as follows. First, a pre-formed pre-laminate consisting of the structural layer 2, acrylic adhesive layer 3 and paper backing 4 is fed to a conveyor that transports the pre-laminate through successive stations of a manufacturing line. The conveyor preferably comprises one or more looped belts, eg of PTFE-coated glass fibre. Suction may be applied from beneath the belts to hold the pre-laminate flat during at least the initial stages of the manufacturing process. The pre-laminate is fed to the belt with the paper backing 4 lowermost, ie with the paper backing 4 in contact with the belt and the surface of the structural layer 2 opposite to that to which the acrylic adhesive 3 is applied uppermost.

At a first station of the manufacturing line, the silicone gel layer 5 is applied. As is conventional, the silicone gel layer 5 is formed by application of a curable mixture of two components via an applicator in which the two components are intimately mixed. Prior to curing, the mixture is fluid and can be applied as a uniform film with the desired thickness. The mixture may be applied by spraying, but more commonly is applied from the edge of a suitably formed blade that is positioned close to the surface of the laminate passing beneath it.

After application of the curable silicone mixture, the coated laminate passes into a first curing stage where the laminate passes beneath a bank of medium wave infra-red heaters that operate continuously. The thermal energy from these heaters initiates curing of the silicone mixture, and in particular cures the upper surface of the mixture, which maintains the structural integrity of the silicone layer during passage of the laminate through a second, longer curing stage. In the second curing stage, the laminate passes beneath further medium wave infra-red heaters. Curing of the silicone mixture, to form a layer of gel of the desired thickness and other properties, is completed during passage of the laminate through the second curing stage. The operating parameters may be optimised to suit the particular product being manufactured. Variables that may be adjusted include the power of the infra-red heaters, the speed of passage through the various stages of the process, as well as the length of the curing stages. Typically, the time taken for the laminate to pass through the curing stages is between 5 and 15 minutes.

At a suitable stage of the process, perforations are introduced into the laminate. This may be achieved by means of pins that reciprocate into and out of the laminate, or which are mounted on a rotating drum.

After completion of curing, the release liner is applied to the exposed surface of the silicone gel layer. This may be achieved by conventional means, involving the feeding of the two components of the release liner from rollers and passing the two components over suitable formers to introduce the fold into the first component 6a and to cause the two components 6a,6b to overlap to the desired extent.

Figure 2:
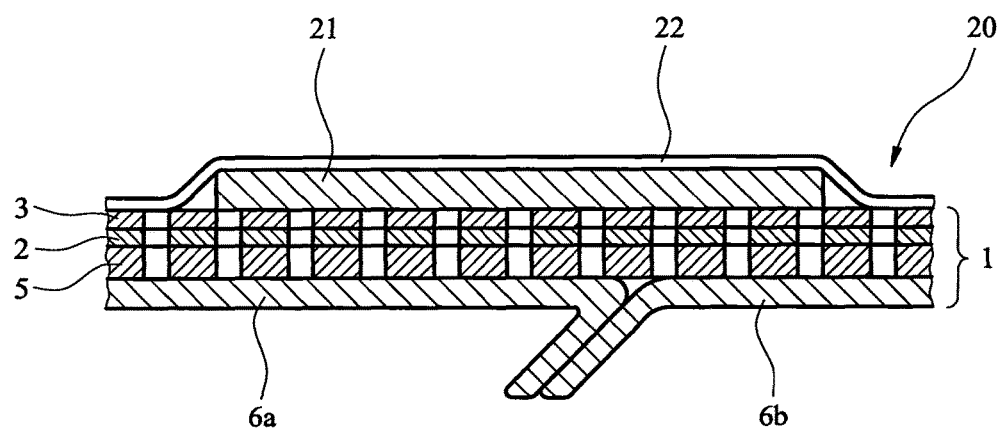
FIG. 2 is a cross-sectional view, again schematic and not to scale, of a first embodiment of a dressing incorporating the laminate of FIG. 1 as a skin contact film.
Figure 3:
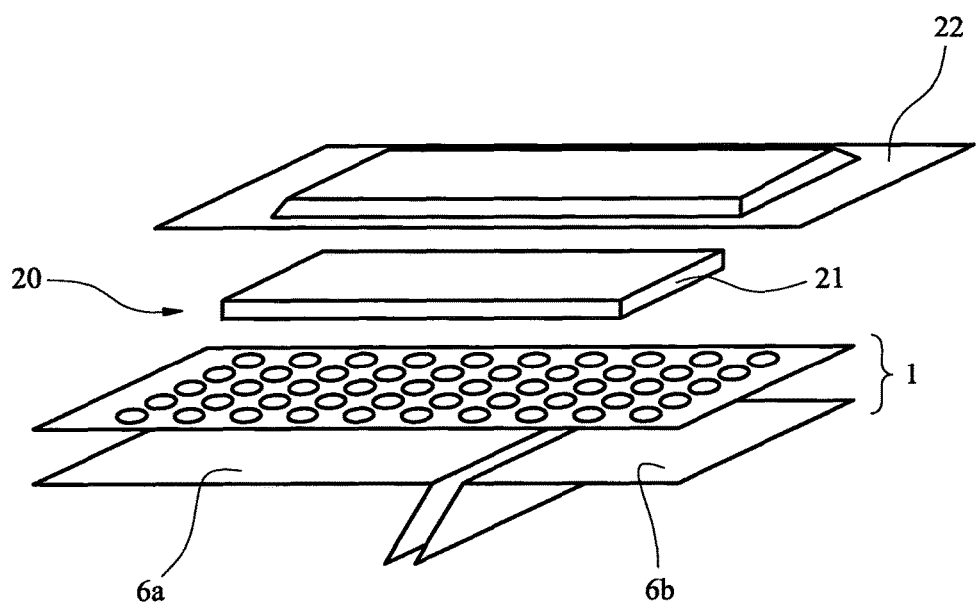
FIG. 3 is an exploded view of the dressing of FIG. 2.

FIG. 2 shows a cross-section, and FIG. 3 an exploded view, of a first embodiment, generally designated 20, of a wound dressing according to the invention, in which the laminate 1 of FIG. 1 is incorporated.

To produce the dressing 20 of FIGS. 2 and 3, the paper backing 4 is stripped off the laminate 1, most conveniently with the laminate 1 inverted relative to its orientation shown in FIG. 1. An absorbent pad 21 is then positioned on the exposed acrylic adhesive layer 3 and a gas-permeable but fluid-impermeable cover sheet 22 is placed over the absorbent pad 21. The cover sheet 22 may be formed from any suitable material, but is generally a synthetic plastics film or laminate, eg a laminate of a nylon material and polyurethane. The cover sheet 22 is pressed into adhesive contact with the acrylic adhesive layer 3 around the periphery of the absorbent pad 21. The cover sheet 22 is applied as a planar sheet but may stretch and deform to fit around the absorbent pad, as indicated in FIG. 3.

Finally, the assembled dressing 20 is completed by cutting to the desired size. It will be appreciated that full-scale manufacture of the dressing 20 would normally involve continuous feed of the laminate 1 to an assembly line, stripping off of the paper backing 4, positioning of absorbent pads 21 and application of the cover sheet 22, followed by cutting of the completed dressings 20 from the continuous material. Passage of the product through the various stages of assembly may be continuous, or it may be intermittent, the product being indexed from one stage to the next.

The assembled dressings 20 will normally be sterile-packaged as individual units. For use, the dressing 20 is removed from its packaging, the release liner 6a,6b removed to expose the silicone gel layer, and the dressing applied to a wound, with the silicone gel layer in contact with the wound. The dimensions of the dressing 20 are chosen such that the entire wound is overlaid by the absorbent pad 21. Wound exudate is able to pass through the perforations 7 in the laminate 1, and is absorbed by the absorbent pad 21. The absorbent pad 21 may comprise a foam or other porous material that is capable of absorbing fluid by capillary or similar action. Alternatively, the absorbent pad 21 may consist of, or comprise, a so-called superabsorbent material, eg based on a hydrogel, that is capable of absorbing aqueous fluid and swelling to several times its original dimensions.

Figure 4:
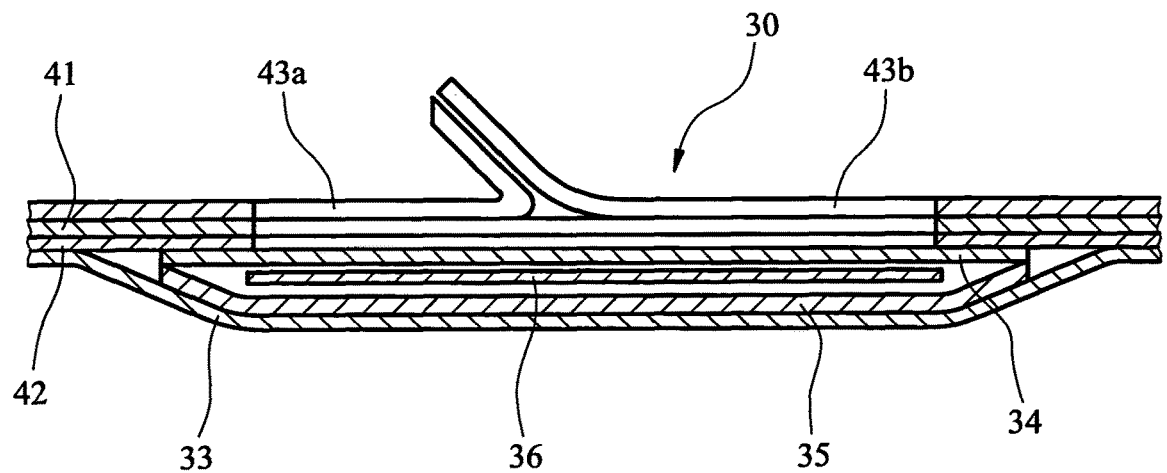
FIG. 4 is a cross-sectional view, again schematic and not to scale, of a second embodiment of a dressing according to the invention, that incorporates a laminate similar to that of FIG. 1 as a skin contact film.
Figure 5:
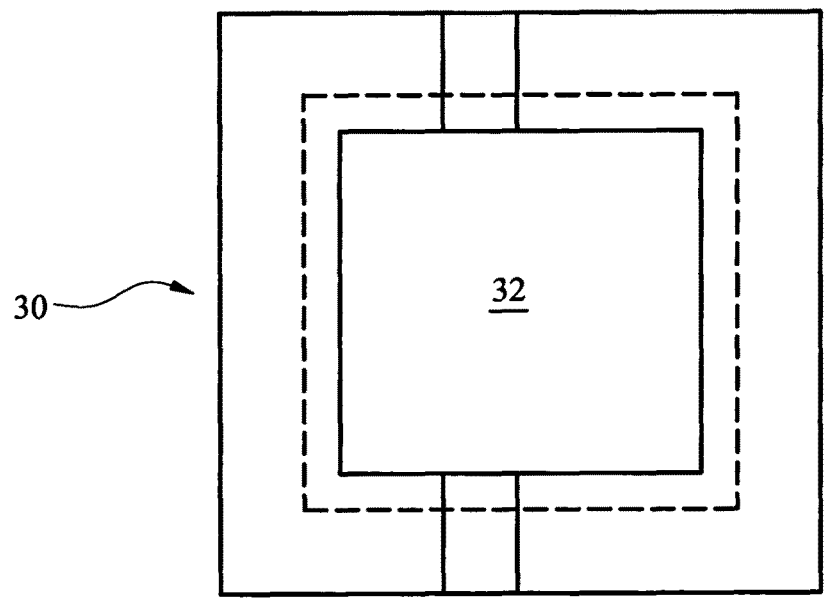
FIG. 5 is an underside plan view of the dressing of FIG. 4.

Turning now to FIGS. 4 and 5, a second embodiment of a wound dressing according to the invention is generally designated 30. The dressing 30 is broadly similar in construction to the first embodiment (FIGS. 2 and 3), but differs therefrom in two principal respects. First, the laminate 31 that constitutes a skin contact film is not formed with a regular array of perforations, but instead has only a single central opening 32, the peripheral part of the skin contact film that surrounds the opening 32 being continuous. Secondly, the absorbent component that is captivated between the peripheral part of the skin contact film and a fluid-impermeable cover sheet 33 is not a simple pad of absorbent material. Instead, the absorbent component comprises an envelope formed from a sheet of a non-woven viscose 34 and a sheet of a nylon-based material 35. The envelope contains an absorbent material in the form of a sheet 36 of superabsorbent material.

The dressing 30 is manufactured in a generally similar manner to the first embodiment 20. The skin contact film 31 is produced by applying a layer of silicone gel 41 to a structural layer 42 that is coated on the other side with a layer of acrylic adhesive that carries a paper backing. Release lines 44a,43b are then applied to the surface of the silicone gel 41. The skin contact film 31 is then fed through an assembly line in which the paper backing is stripped off the acrylic adhesive, the opening 32 is cut and the preformed envelope containing the absorbent material is positioned over the opening 32. The cover sheet 33 is then pressed into contact with the acrylic adhesive, thereby captivating the envelope between the cover sheet and the skin contact film. As for the first embodiment 20, the manufacturing process is normally a continuous process that involves continuous feed of the skin contact film 31 to an assembly line, stripping off of the paper backing, positioning of the envelopes of absorbent material and application of the cover sheet 33, followed by cutting of the completed dressings 30 from the continuous material. Passage of the product through the various stages of assembly may be continuous, or it may be intermittent, the product being indexed from one stage to the next.

Figure 6:
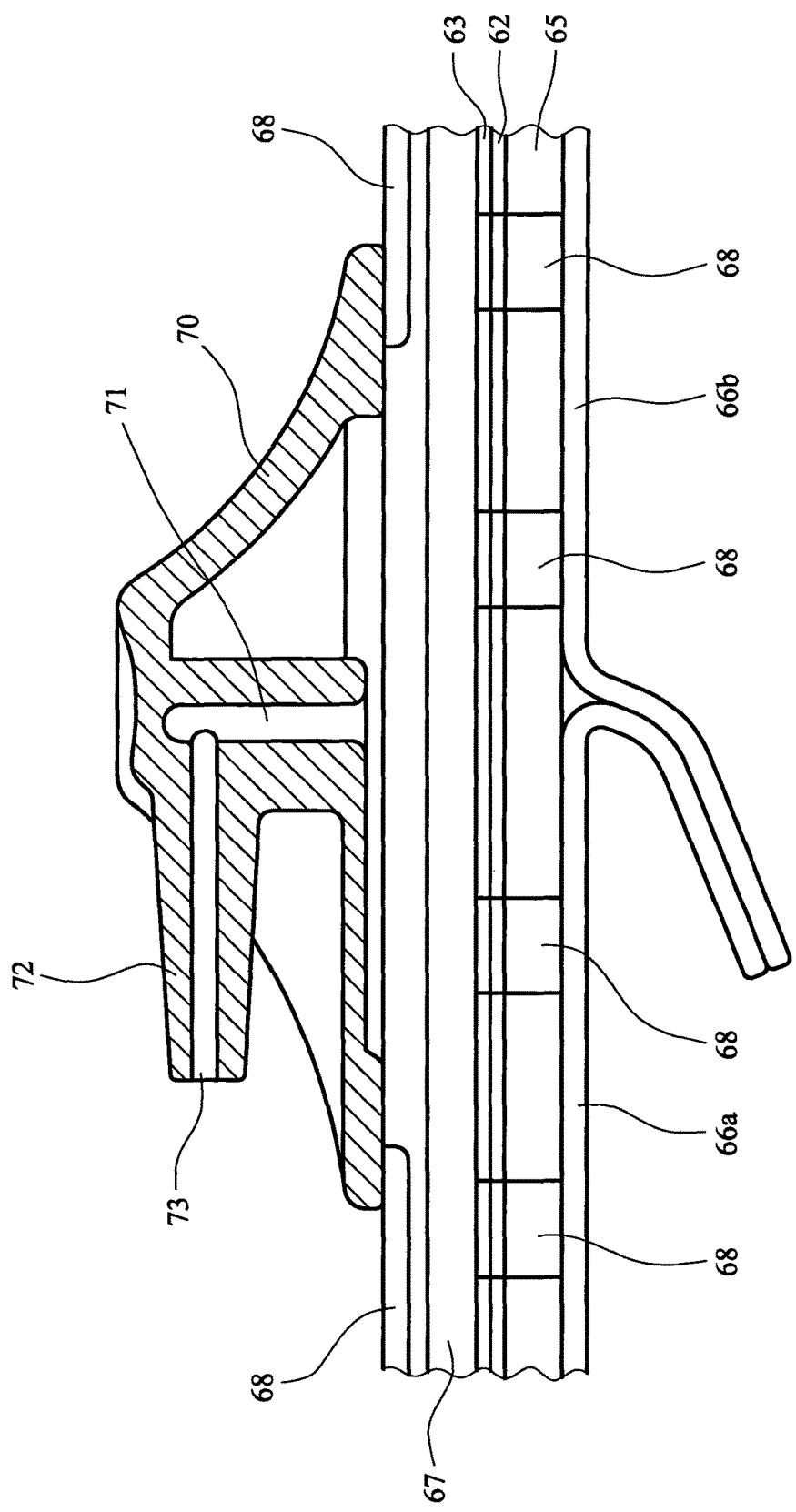
FIG. 6 is a partial cross-sectional view of a third embodiment of a dressing according to the invention, which dressing is provided with a coupling for connection to a gas or suction line.

Referring now to FIG. 6, a third embodiment of a composite wound dressing according to the invention is broadly similar in construction to the embodiment of FIGS. 2 and 3. The dressing comprises a structural layer 62 of melt-blown polyurethane, one side of which is coated with a layer of silicone gel 65 and the other side of which carries a layer of acrylic pressure-sensitive adhesive 63. An absorbent pad 67 is affixed to the acrylic adhesive 63. A fluid-impermeable barrier layer 68 covers the absorbent pad 67 and is bonded to the acrylic adhesive 63 around the periphery of the pad 67 (not visible in FIG. 6). A release liner in two parts 66a,66b overlies the layer of silicone gel 65. Perforations 68 are formed in the layers of silicone gel 65, the structural layer 62 and the acrylic adhesive 63.

The embodiment of FIG. 6 differs from that of FIGS. 2 and 3 in that an opening is formed in the barrier layer 68 and a coupling 70 is bonded to the periphery of that opening. The coupling 70 is injection moulded in rigid plastics material and is generally conical in form. The coupling 70 has an open base and a hollow interior with an upwardly-extending blind bore 71. A tubular extension 72 extends from the body of the coupling 70, generally parallel to the surface of the barrier layer 68. The extension 72 has a bore 73 that opens into the upwardly-extending blind bore 71.

In use, the release liner 66a,66b is removed and the dressing applied to a wound, as for the other embodiments described above. A gas supply line can be connected to the extension 72 in order for air or oxygen to be supplied under slight positive pressure to the interior of the dressing. Alternatively, reduced pressure may be applied to the coupling in order to draw excess fluid from the interior of the dressing.

The laminate 1 of FIG. 1 may also be used in a variety of other applications. For instance, a patch of the laminate 1 may be applied to an item intended to be secured to a hard surface, by removal of the paper backing 4 and application of the exposed pressure-sensitive adhesive 3 to the item concerned. Removal of the release liner 6a,6b then exposes the silicone gel layer 5 which may be used for the releasable adherent and/or non-slip fixation of the item on a surface. Alternatively, a patch of the laminate 1 may be applied to the hard surface and the item then placed onto that pad.

Figure 7:
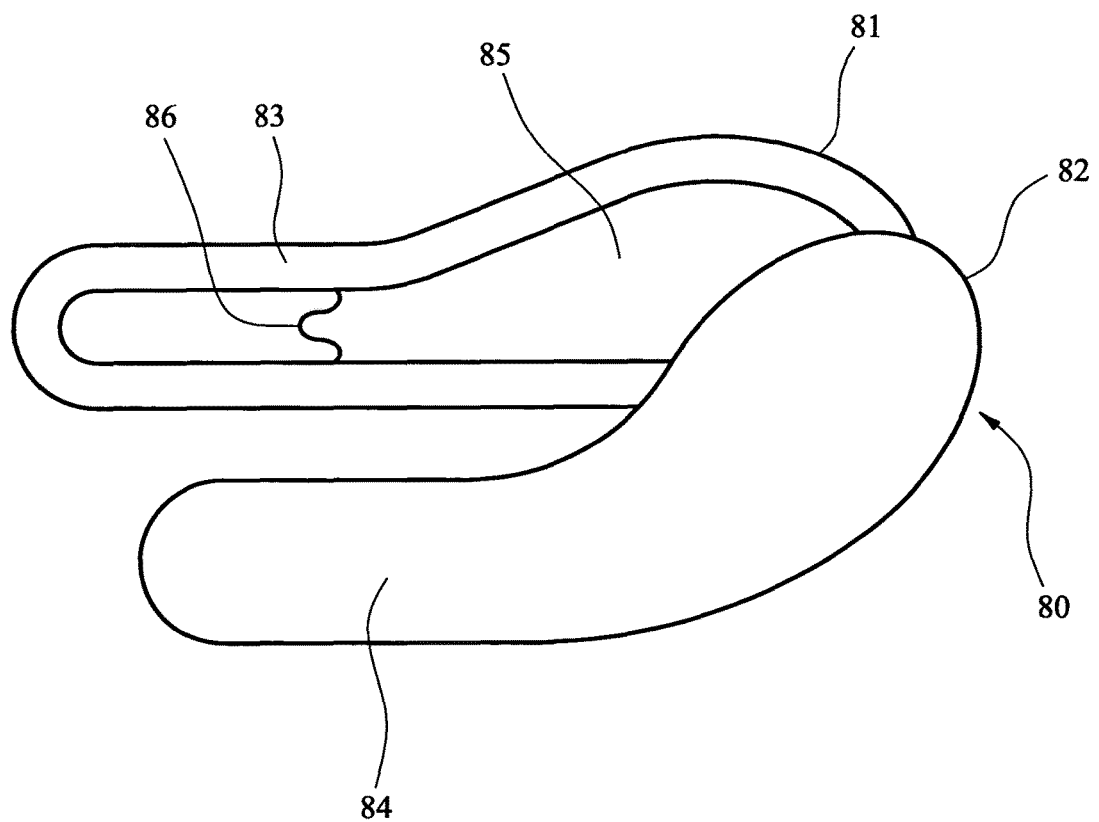
FIG. 7 is a schematic view, from behind and to one side, of a strapless, backless bra incorporating patches of a laminate according to the invention.

The laminate 1 may also be used to secure items other than dressings to the skin. As described above, such items may include items of clothing, in particular items of underwear. Thus, for instance, a patch of the laminate 1 may be applied via the pressure-sensitive adhesive 3 to a strapless and/or backless bra in order to affix the bra to the wearer's skin. An example of such an application is illustrated in FIG. 7, which shows a strapless, backless bra 80. The bra 80 has a generally conventional form, comprising a pair of cups 81,82 from which extend lateral wings 83,84. Two patches of laminate 85 (only one of which is visible in FIG. 7) are applied to the internal, body-facing surface of the bra 80, each patch 85 covering the majority of the internal surface of a cup 81,82 and the wing 83,84 that extends therefrom. The acrylic adhesive on the rear (as viewed in FIG. 7) of the patches 85 adheres each patch to the internal surface of the bra 80. Each patch 85 is covered by a release liner formed in two parts that overlap to form tabs 86 by which the release liner can be removed. In use, the release liners are removed from each patch 85, exposing the silicone gel. The bra 80 may then be applied to the user's breasts, with the wings 83,84 extending around the torso, beneath the arms. The bra 80 is retained in position by the adherence of the silicone gel to the skin, but may be easily and comfortably removed and repositioned if desired.

The invention claimed is:

1. A method for the manufacture of a wound dressing comprising a skin contact layer in the form of a releasably adhesive laminate comprising a melt-blown structural layer carrying on at least part of only one side thereof a silicone gel and carrying on at least part of the other side thereof a pressure-sensitive adhesive, which method comprises:
    a) providing a preformed pre-laminate comprising the melt-blown structural layer carrying the pressure-sensitive adhesive on one side;
    b) applying directly to the other side of the melt-blown structural layer a curable liquid silicone gel precursor composition comprising vinyl-substituted silicone and a hydride-containing silicone; and
    c) causing or allowing the silicone gel precursor composition to cure, thereby forming a layer of silicone gel in direct contact with the melt-blown structural layer.

2. The method as claimed in claim 1, wherein the melt-blown structural layer is a melt-blown polyurethane structural layer.

3. The method as claimed in claim 1, wherein the pressure-sensitive adhesive is an acrylic adhesive.

4. The method as claimed in claim 1, wherein the silicone gel is coated onto the structural layer at a coating weight of between 50 g/m$^2$ and 800 g/m$^2$.

5. The method as claimed in claim 1, wherein the thickness of the silicone gel layer is between 5 μm and 10 mm.

6. The method as claimed in claim 1, further comprising a step of introducing perforations into the laminate.

7. The method as claimed in claim 6, wherein the perforations are arranged in a regular array.

8. The method as claimed in claim 6, wherein the perforations are circular and have a diameter of from 50 μm to 10 mm.

9. The method as claimed in claim 1, further comprising a step of affixing one or more secondary dressing components to the laminate via the pressure-sensitive adhesive.

10. The method as claimed in claim 9, wherein the one or more secondary dressing components include one or more absorbent components.

11. The method as claimed in claim 10, wherein the one or more absorbent components are selected from fabric pads, hydrophilic foams, hydrogels, hydrocolloids, and alginates.

\* \* \* \* \*